(12) United States Patent  (10) Patent No.: US 7,988,623 B2
Pagliuca et al.  (45) Date of Patent: Aug. 2, 2011

(54) APPARATUS AND METHODS FOR SHIELDING BODY STRUCTURES DURING SURGERY

(75) Inventors: James J. Pagliuca, Millis, MA (US); Gene P. DiPoto, Upton, MA (US)

(73) Assignee: Zimmer Spine, Inc., Minneapolis, MN (US)

( * ) Notice: Subject to any disclaimer, the term of this patent is extended or adjusted under 35 U.S.C. 154(b) by 1464 days.

(21) Appl. No.: 11/421,044

(22) Filed: May 30, 2006

(65) Prior Publication Data

US 2007/0016223 A1  Jan. 18, 2007

Related U.S. Application Data

(62) Division of application No. 10/280,799, filed on Oct. 25, 2002, now abandoned.

(51) Int. Cl.
*A61B 1/32* (2006.01)
(52) U.S. Cl. ......................................... 600/201; 606/190
(58) Field of Classification Search .................... 606/86, 606/87, 108, 213, 190, 198; 600/201; 604/104, 604/264
See application file for complete search history.

(56) References Cited

U.S. PATENT DOCUMENTS

| | | |
|---|---|---|
| 465,161 A | 12/1891 | Chase |
| 2,605,582 A | 8/1952 | Allen |
| 3,044,461 A | 7/1962 | Murdock |
| 3,789,852 A | 2/1974 | Kim et al. |
| 4,258,716 A | 3/1981 | Sutherland |
| 4,545,374 A | 10/1985 | Jacobson |
| 4,601,713 A | 7/1986 | Fuqua |
| 4,716,901 A | 1/1988 | Jackson et al. |
| 4,819,620 A | 4/1989 | Okutsu |
| 4,863,133 A | 9/1989 | Bonnell |
| 4,921,478 A | 5/1990 | Solano et al. |
| 4,984,564 A | 1/1991 | Yuen |
| 5,020,519 A | 6/1991 | Hayes et al. |
| 5,025,778 A | 6/1991 | Silverstein et al. |
| 5,131,382 A | 7/1992 | Meyer |
| 5,139,499 A | 8/1992 | Small et al. |
| 5,163,949 A | 11/1992 | Bonutti |

(Continued)

FOREIGN PATENT DOCUMENTS

EP  0 528 562  2/1993

(Continued)

OTHER PUBLICATIONS

International Search Report, dated Jul. 2, 2004 for counterpart PCT application No. PCT/US2003/28286.

(Continued)

*Primary Examiner* — Michael J Milano
*Assistant Examiner* — Victor X Nguyen
(74) *Attorney, Agent, or Firm* — Seager, Tufte & Wickhem LLC

(57) ABSTRACT

An apparatus for shielding a body structure during surgical procedures which is configured for insertion into the internal passage of a support structure, and includes an elongated body portion with a distal tip portion configured to cover the body structure without substantially displacing the body structure. The apparatus also includes a mounting portion at a proximal end portion thereof for mounting the apparatus within the internal passage of the support structure, and a member connected to the mounting portion to release the mounting portion with respect to the internal passage of the wall portion.

33 Claims, 13 Drawing Sheets

U.S. PATENT DOCUMENTS

| | | |
|---|---|---|
| 5,171,279 A | 12/1992 | Mathews |
| 5,190,050 A | 3/1993 | Nitzsche |
| 5,190,561 A | 3/1993 | Graber |
| 5,195,541 A | 3/1993 | Obenchain |
| 5,197,971 A | 3/1993 | Bonutti |
| 5,224,680 A | 7/1993 | Greenstein et al. |
| 5,287,845 A | 2/1994 | Faul et al. |
| 5,295,994 A | 3/1994 | Bonutti |
| 5,312,417 A | 5/1994 | Wilk |
| 5,345,927 A | 9/1994 | Bonutti |
| 5,354,302 A | 10/1994 | Ko |
| 5,370,647 A | 12/1994 | Graber et al. |
| 5,395,317 A | 3/1995 | Kambin |
| 5,439,464 A | 8/1995 | Shapiro |
| 5,454,365 A | 10/1995 | Bonutti |
| 5,472,426 A | 12/1995 | Bonati et al. |
| 5,474,558 A | 12/1995 | Neubardt |
| 5,484,437 A | 1/1996 | Michelson |
| 5,489,307 A | 2/1996 | Kuslich et al. |
| 5,520,607 A | 5/1996 | Frassica et al. |
| 5,571,072 A | 11/1996 | Kronner |
| 5,575,754 A | 11/1996 | Konomura |
| 5,601,590 A | 2/1997 | Bonutti et al. |
| 5,667,520 A | 9/1997 | Bonutti |
| 5,707,359 A | 1/1998 | Bufalini |
| 5,720,751 A | 2/1998 | Jackson |
| 5,782,831 A | 7/1998 | Sherman et al. |
| 5,792,044 A | 8/1998 | Foley et al. |
| 5,795,289 A | 8/1998 | Wyttenbach |
| 5,827,319 A | 10/1998 | Carlson et al. |
| 5,902,231 A | 5/1999 | Foley et al. |
| 5,910,141 A | 6/1999 | Morrison et al. |
| 5,954,635 A | 9/1999 | Foley et al. |
| 5,961,499 A | 10/1999 | Bonutti et al. |
| 5,976,146 A * | 11/1999 | Ogawa et al. ............... 606/86 R |
| 5,997,508 A | 12/1999 | Lunn et al. |
| 6,007,487 A | 12/1999 | Foley et al. |
| 6,051,001 A | 4/2000 | Borghi |
| 6,096,038 A | 8/2000 | Michelson |
| 6,120,437 A | 9/2000 | Yoon et al. |
| 6,162,236 A | 12/2000 | Osada |
| 6,171,299 B1 | 1/2001 | Bonutti |
| 6,187,000 B1 | 2/2001 | Davison et al. |
| 6,251,111 B1 | 6/2001 | Barker et al. |
| 6,267,763 B1 | 7/2001 | Castro |
| 6,306,170 B2 | 10/2001 | Ray |
| 6,312,443 B1 | 11/2001 | Stone |
| 6,338,730 B1 | 1/2002 | Bonutti et al. |
| 6,358,266 B1 | 3/2002 | Bonutti |
| 6,361,488 B1 | 3/2002 | Davison et al. |
| 6,371,968 B1 | 4/2002 | Kogasaka et al. |
| 6,383,195 B1 | 5/2002 | Richard |
| 6,425,859 B1 | 7/2002 | Foley et al. |
| 6,494,893 B2 | 12/2002 | Dubrul et al. |
| 6,497,654 B1 | 12/2002 | Leonard et al. |
| 6,500,206 B1 | 12/2002 | Bryan |
| 6,524,320 B2 | 2/2003 | DiPoto |
| 6,530,880 B2 | 3/2003 | Pagliuca |
| 6,530,926 B1 | 3/2003 | Davison |
| 6,564,078 B1 | 5/2003 | Marino et al. |
| 6,652,553 B2 | 11/2003 | Davison et al. |
| 7,187,000 B2 | 3/2007 | Yang et al. |
| 2001/0011170 A1 | 8/2001 | Davison et al. |
| 2002/0002360 A1 | 1/2002 | Orth et al. |
| 2003/0009130 A1 | 1/2003 | Stecker et al. |
| 2003/0014068 A1 | 1/2003 | Bonutti et al. |
| 2003/0040656 A1 | 2/2003 | Pagliuca et al. |
| 2003/0073998 A1 | 4/2003 | Pagliuca et al. |
| 2003/0139648 A1 | 7/2003 | Foley et al. |
| 2003/0153927 A1 | 8/2003 | DiPoto et al. |
| 2003/0191371 A1 | 10/2003 | Smith et al. |
| 2003/0195405 A1 | 10/2003 | Marino et al. |
| 2003/0195493 A1 | 10/2003 | Davison et al. |
| 2003/0195549 A1 | 10/2003 | Davison et al. |
| 2003/0195550 A1 | 10/2003 | Davison et al. |
| 2003/0195551 A1 | 10/2003 | Davison et al. |
| 2003/0199871 A1 | 10/2003 | Foley et al. |
| 2003/0199885 A1 | 10/2003 | Davison et al. |
| 2004/0059339 A1 | 3/2004 | Roehm, III et al. |
| 2004/0078051 A1 | 4/2004 | Davison et al. |
| 2004/0093002 A1 | 5/2004 | Davison et al. |
| 2004/0098012 A1 | 5/2004 | Davison et al. |

FOREIGN PATENT DOCUMENTS

| | | |
|---|---|---|
| EP | 0 807 415 | 11/1997 |
| EP | 0 980 677 | 2/2000 |
| EP | 1 305 077 | 5/2003 |
| FR | 2 701 379 | 8/1994 |
| JP | 2000083960 A2 | 3/2000 |
| JP | 2001149376 A2 | 6/2001 |
| TW | 137324 | 7/1990 |
| TW | 141205 | 9/1990 |
| WO | WO 92/21292 | 2/1992 |
| WO | WO 93/14801 | 8/1993 |
| WO | WO 94/03114 | 2/1994 |
| WO | WO 95/10218 | 4/1995 |
| WO | WO 95/32663 | 12/1995 |
| WO | WO 03/007783 | 2/2000 |
| WO | WO 01/54560 | 8/2001 |
| WO | WO 02/09801 | 2/2002 |
| WO | WO 02/078767 | 10/2002 |
| WO | WO 2004/021899 | 3/2004 |
| WO | 2004039235 | 5/2004 |

OTHER PUBLICATIONS

English translation of Taiwanese Intellectual Property Office Official Letter referring to TW 137324 and TW 141205.

* cited by examiner

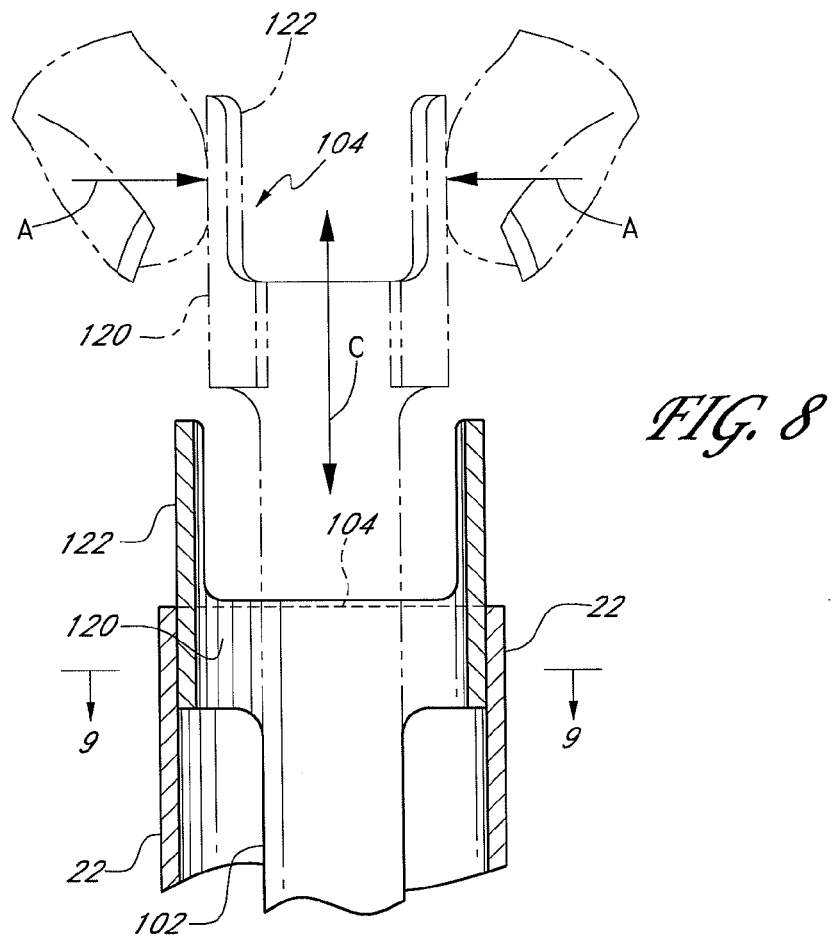
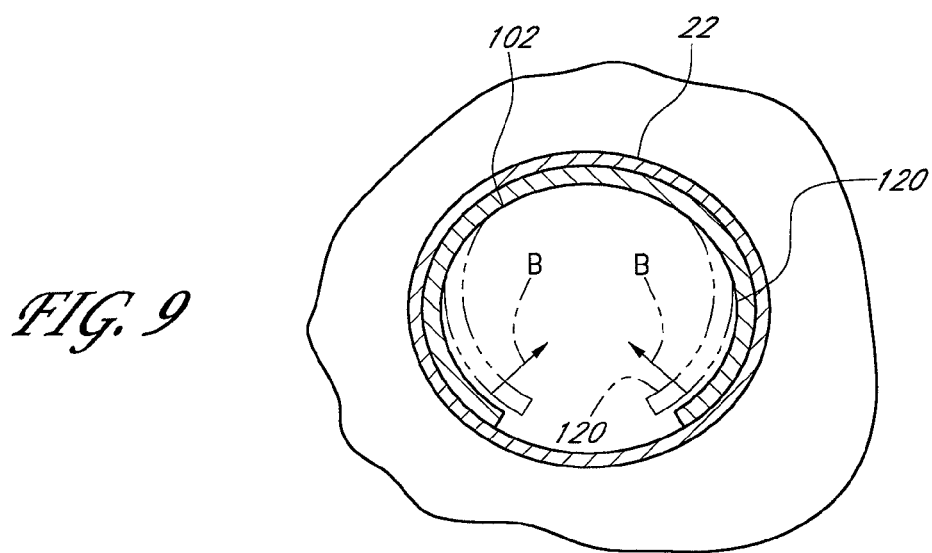

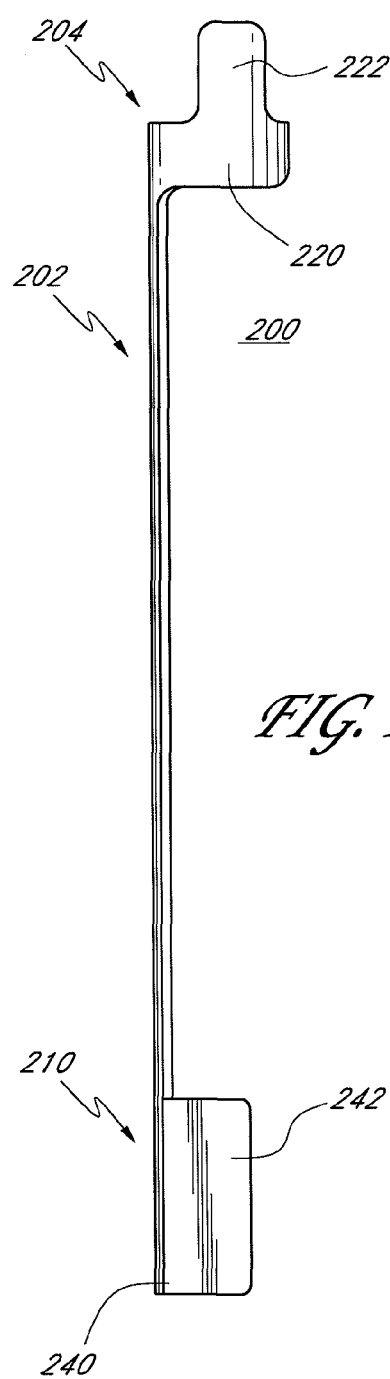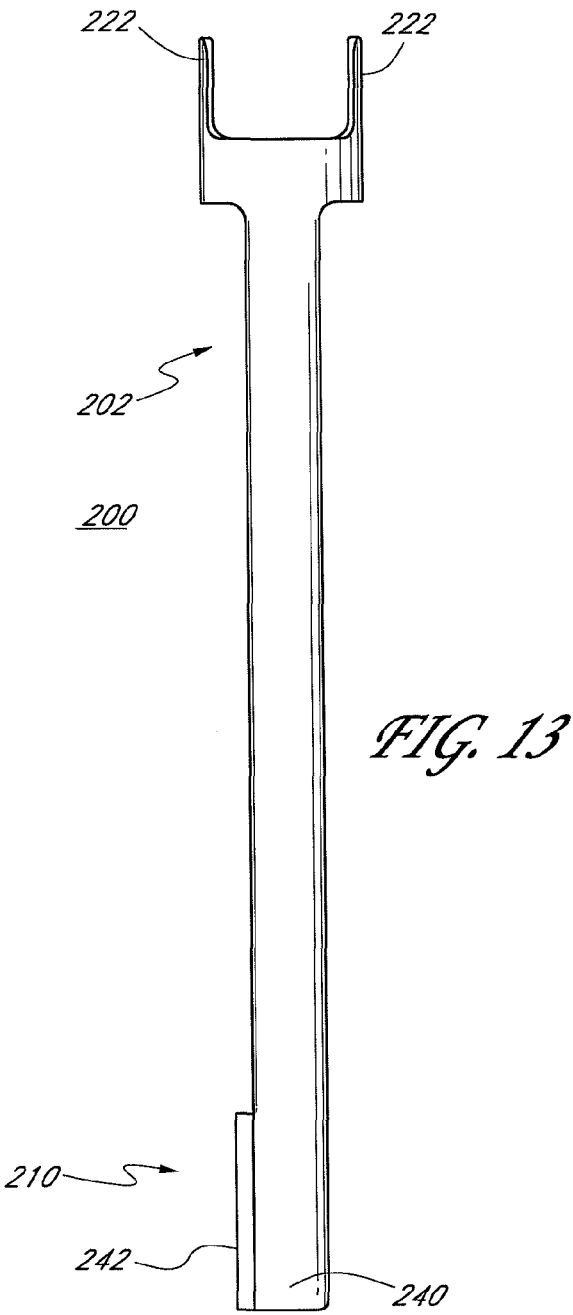

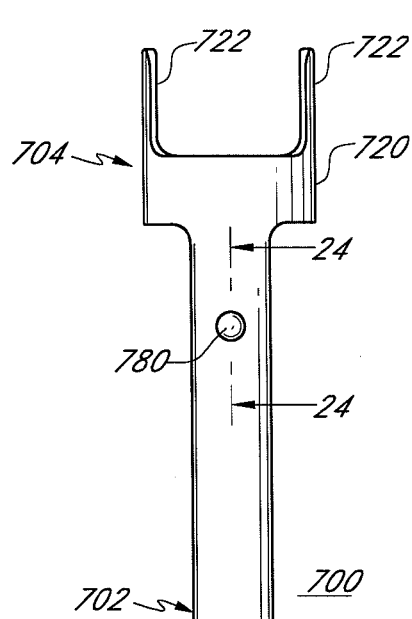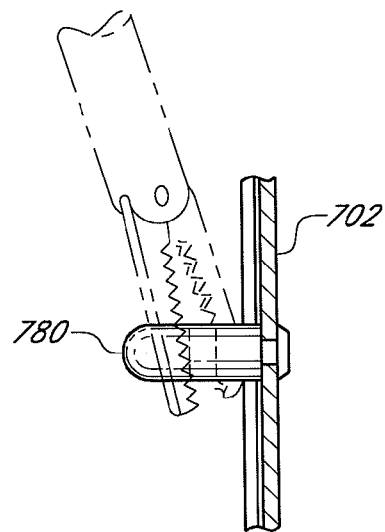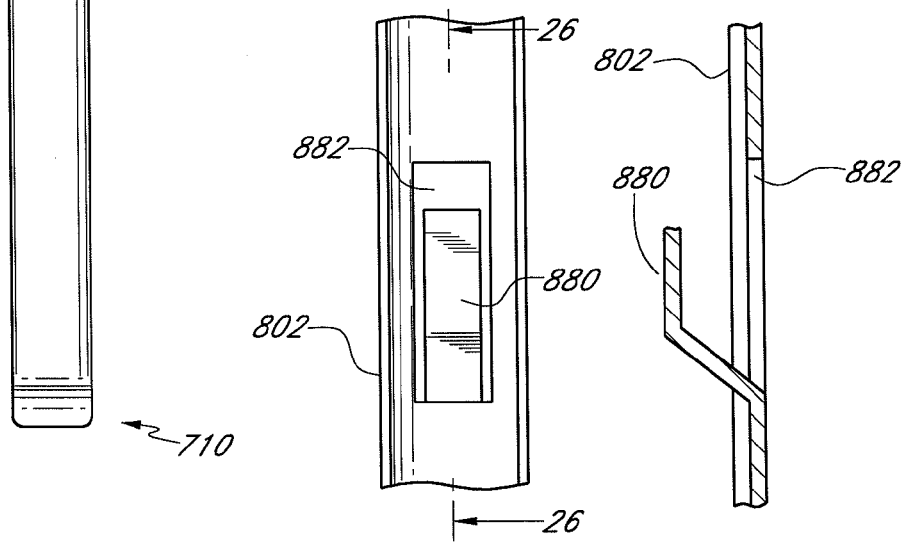
FIG. 23   FIG. 24   FIG. 25   FIG. 26

APPARATUS AND METHODS FOR SHIELDING BODY STRUCTURES DURING SURGERY

CROSS-REFERENCE TO RELATED APPLICATIONS

This application is a divisional application of U.S. application Ser. No. 10/280,799, filed Oct. 25, 2002, now abandoned, which is hereby incorporated by reference in its entirety and should be considered a part of this specification.

BACKGROUND OF THE INVENTION

1. Field of the Invention

This invention relates to methods and apparatus for performing minimally invasive surgery, and more particularly to instruments for protecting body structures in a patient.

2. Background Information

Spinal surgery presents significant difficulties to the surgeon attempting to reduce chronic back pain or correct spinal deformities without introducing additional trauma due to the surgical procedure itself. In order to access the vertebrae to perform spinal fixation, discectomy or related procedures, the surgeon is typically required to make large incisions and cut or strip muscle tissue surrounding the spine. During these procedures, care must be taken not to injure nerve tissue in the area.

Apparatus for performing minimally invasive techniques have been proposed to reduce the trauma of posterior spinal surgery by reducing the size of the incision and the degree of muscle stripping in order to access the vertebrae. U.S. Pat. No. 6,187,000 to Davison et al., entitled "Cannula for Receiving Surgical Instruments," discloses a novel cannula or retractor which receives surgical instruments for performing a surgical procedure on a body. The cannula or retractor includes an expandable portion for enabling an increase in the cross-sectional area of the passage at the distal end. The expandable portion of the tube structure, when expanded, provides an enlarged operative space.

Such minimally invasive techniques provide significant advantages in terms of reduced blood loss and trauma. The '000 patent describes a novel device which provides improved access over prior art cannulas. Nevertheless, any minimally invasive procedure provides diminished access when compared with traditional open procedures. The presence of delicate nerve tissue in the spinal region, especially when interbody fusion procedures are being performed, requires extra care on the part of the surgeon to avoid damaging such tissues.

U.S. Pat. Nos. 6,425,859 and 6,007,487 to Foley et al. describe a retractor for manipulating through tissue. The retractor provides no mechanism for releasably mounting the retractor with respect to a cannula, so that the retractor can be released and removed from the cannula without disturbing the cannula, or other instrumentation positioned therein. Moreover, the primary function of the device described in the 859 and 487 patents is retraction of tissues rather than protection of the nerve and dura.

Accordingly, there is a need in the art for an apparatus and a method of surgery to protect such body tissues, while still affording good visibility, and which is easily positionable.

SUMMARY OF THE INVENTION

An object of the present invention is to provide access and visibility to perform minimally invasive surgical procedures.

Another object of the present invention is to provide apparatus for protecting delicate body tissue during conventional and minimally invasive procedures.

A further object of the invention is to provide apparatus which is self-supporting during the surgical procedure.

A still further object of the invention is to provide apparatus which may be releasably mounted and repositioned without disturbing other apparatus.

These and other objects of the invention, which will become apparent with reference to the disclosure herein, are accomplished by an apparatus and method for shielding a body structure during surgical procedures. A shield apparatus is configured for insertion into an internal passage of a support structure. The shield apparatus comprises an elongated body portion comprising a distal tip portion configured to cover the body structure without substantially displacing the body structure, a mounting portion at a proximal end portion thereof for mounting the apparatus within the internal passage of the support structure; and a member associated with the mounting portion to release the mounting portion with respect to the internal passage of the support structure. The apparatus may further comprise a conduit comprising a wall portion defining an internal passage therethrough for percutaneous insertion into the body tissue.

In one embodiment, the mounting portion comprises a ring-shaped configuration defining a gap. The mounting portion may be fabricated from a resilient material that is movable between a first configuration having a first outer dimension and a second configuration having a second, reduced outer dimension. The member for releasing the mounting member may comprise a pair of finger grips extending from the ring-shaped portion for deforming the mounting portion to the second configuration. In another embodiment, the mounting portion may comprise a flange, an O-ring, or a bumper member extending from the ring-shaped portion which engages the internal passage of the wall portion. The elongated body portion may be a substantially flat, rectangular member, or a rod. The apparatus may further comprise a handle portion extending from a proximal end thereof.

The body structure may be a nerve located adjacent vertebral tissue, and the distal tip portion may be configured to cover the nerve root without substantially displacing the nerve root. Alternatively, the body structure is the dura, and the distal tip portion is configured to cover the dura without substantially displacing the dura. In yet another embodiment, the body structure is the dura and adjacent vertebra, and the distal tip portion is configured to be positioned adjacent the dura and between the vertebrae to define a space for receiving material therein.

In another embodiment, the distal tip portion comprises a pair of surfaces defining an angle therebetween. According to this embodiment, the distal tip portion is configured to engage both the nerve root and the dura. The angle between the pair of distal surfaces may be about 45 degrees to about 90 degrees.

A method for performing a surgical procedure on a patient comprises percutaneously inserting a conduit comprising a wall portion defining an internal passage therethrough into the body tissue. A further step is to provide an apparatus comprising a body portion having a distal tip portion configured to cover a body structure and a proximal mounting portion. A next step is to insert the apparatus through the conduit. The distal end portion of the apparatus is positioned adjacent the body tissue without substantially displacing the body tissue. The proximal portion is releasably mounted with respect to the stationary mounting structure.

In one embodiment of the method, the step of inserting the apparatus through the conduit and positioning the distal tip portion of the apparatus adjacent the body tissue comprises positioning the distal tip portion adjacent to the dura without substantially displacing the dura. In another embodiment of the method, the step of inserting the apparatus through the conduit and positioning the distal tip portion of the apparatus adjacent the body tissue comprises positioning the distal tip portion adjacent to the nerve root without substantially displacing the nerve. In yet another embodiment of the method, the step of the step of inserting the apparatus through the conduit and positioning the distal tip portion of the apparatus adjacent the body tissue comprises positioning the distal tip portion adjacent the dura and between the vertebrae to define a space for receiving material therein.

Advantageously, the step of providing an apparatus comprises providing a member extending from the mounting portion to release the mounting portion with respect to the internal passage of the wall portion. The method may further comprise the step of releasing the mounting portion with respect to the internal passage of the wall portion. The step of providing an apparatus may comprise providing the mounting member having a ring-shaped structure and being resiliently movable between a first configuration having a first outer dimension and a second configuration having a second, reduced outer dimension, and a member comprising a pair of finger grips extending from the ring-shaped portion for deforming the mounting portion to the deformed configuration. The step of releasably mounting the proximal portion with respect to the internal passage of the wall portion may comprise releasing the finger grips to allow the ring-shaped structure to move towards the first configuration. The step of releasing the mounting portion with respect to the internal passage of the wall portion may comprise compressing the finger grips to move the ring-shaped structure to towards the second configuration.

In a further embodiment, the step of percutaneously inserting the conduit may further comprise moving the wall portion to a configuration having an enlarged cross-sectional area at the distal portion of the conduit.

In another embodiment, the method may further comprise the steps of providing a tab portion extending from the elongated body portion of the apparatus and engaging the tab portion with a surgical instrument inserted into the conduit to remotely reposition the distal end portion of the apparatus.

In accordance with the invention, the objects of providing a system for covering a delicate body structure that is releasable from a support structure, and which does not impede visibility, has been met. Further features of the invention, its nature and various advantages will be more apparent from the accompanying drawings and the following detailed description of illustrative embodiments.

BRIEF DESCRIPTION OF THE DRAWINGS

Further objects, features and advantages of the invention will become apparent from the following detailed description taken in conjunction with the accompanying figures showing illustrative embodiments of the invention, in which:

FIG. 8 is a longitudinal sectional view of the apparatus of FIG. 7 taken from line-8-8 of FIG. 7 in accordance with the present invention.

FIG. 9 is a transverse sectional view of the apparatus of FIG. 8 taken from line-9-9 of FIG. 8 in accordance with the present invention.

FIG. 11(*a*) is a transverse sectional view of the apparatus of FIG. 11, taken along lines 11(*a*)-11(*a*) of FIG. 11, in accordance with the present invention.

FIG. 12 is a side view, similar to FIG. 2, of another embodiment of an apparatus, in accordance with the present invention.

FIG. 13 is a front view, similar to FIG. 5, of the embodiment of FIG. 12, in accordance with the present invention.

FIG. 23 is a front view of another embodiment of the apparatus in accordance with the present invention.

FIG. 24 is a sectional view taken along lines 24-24 of FIG. 23 in accordance with the invention.

FIG. 25 is front view of a portion of another embodiment of the apparatus in accordance with the present invention.

FIG. 26 is a sectional view taken along line 26-26 of FIG. 25, of another embodiment of the apparatus in accordance with the present invention.

Figure 1:
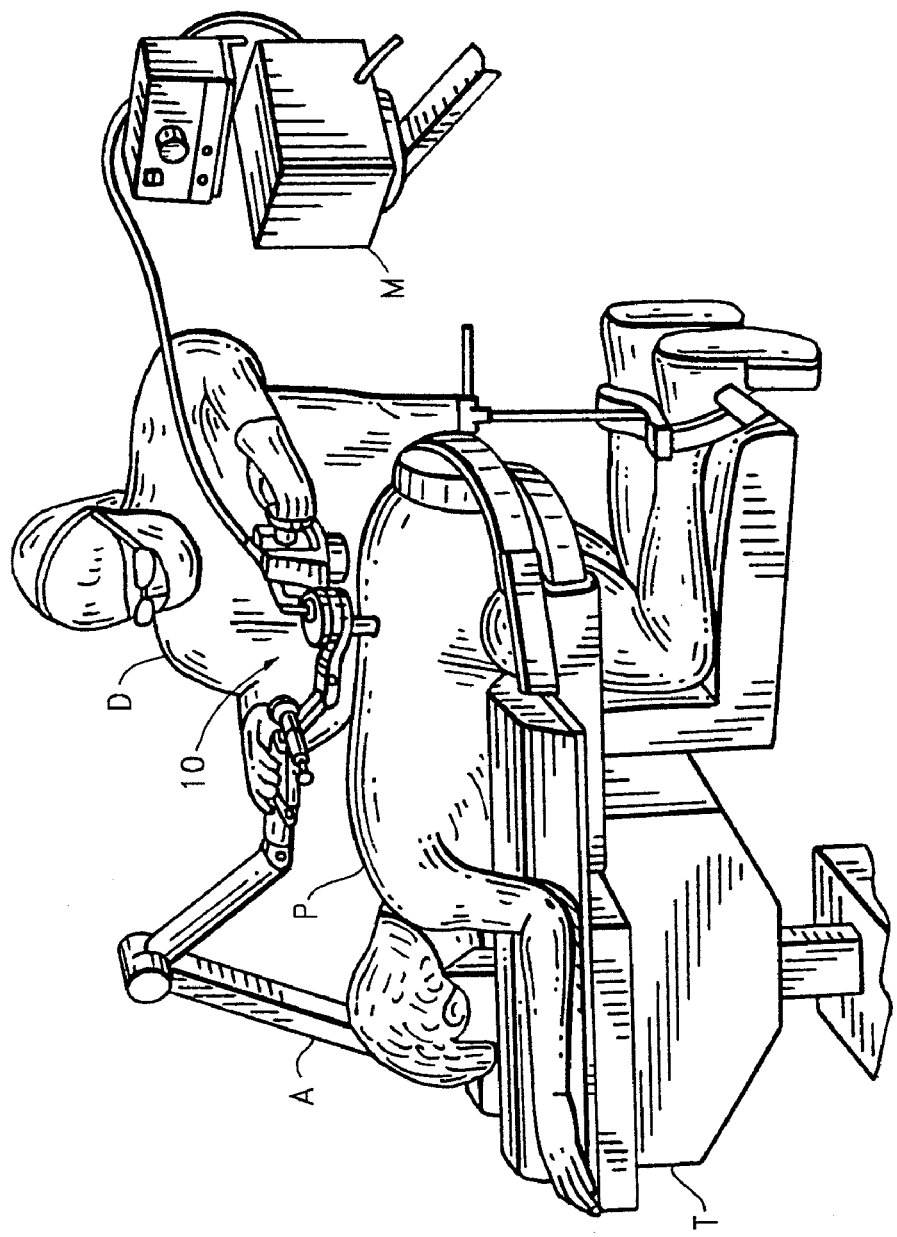
FIG. 1 is a perspective view of the surgical system and procedure in accordance with the present invention.
Figure 2:
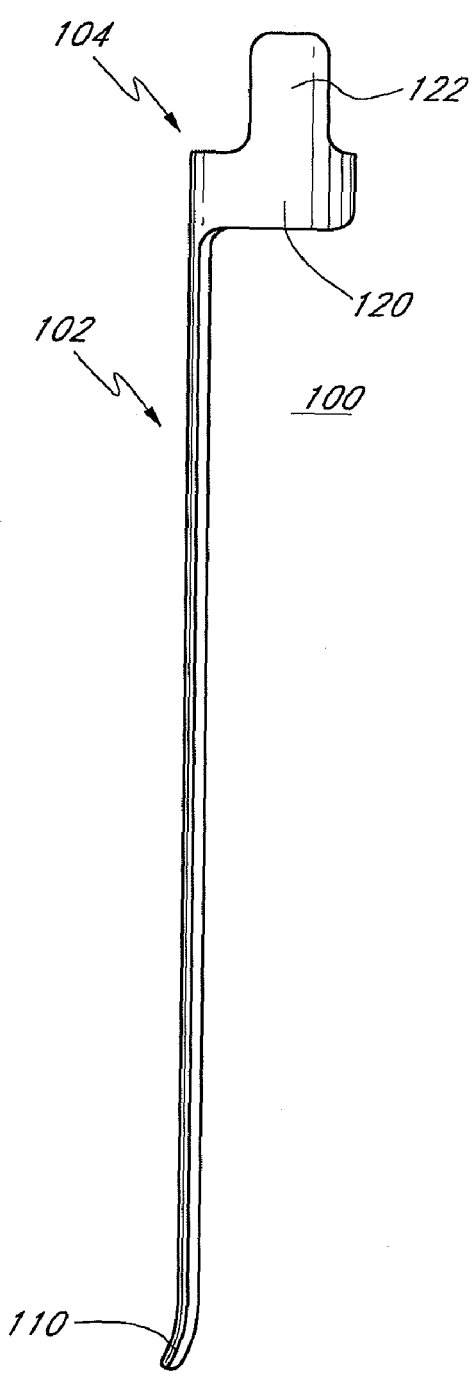
FIG. 2 is a side view of an apparatus in accordance with the present invention.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF THE PREFERRED EMBODIMENTS

The exemplary embodiment of apparatus and procedures described herein will be discussed in terms of endoscopic and minimally invasive procedures and apparatus. However, many aspects of the present invention may find use in conventional, open procedures. In the drawings and description which follows, the term "proximal," as is traditional, refers to the end portion of the apparatus which is closest to the operator, while the term "distal" will refer to the end portion which is furthest from the operator.

Referring now in detail to the drawings, FIG. 1 illustrates an exemplary arrangement for performing the procedure in accordance with the invention. The patient P is typically placed in the prone position on operating table T, taking care that the abdomen is not compressed and physiological lordosis is preserved, as is known in the art. The surgeon D is able to access the surgical site and perform the surgical procedure with the components of the system 10, which will be described in greater detail herein. The system 10 may be supported, in part, by a mechanical support arm A, such as the type generally disclosed in U.S. Pat. No. 4,863,133, which is incorporated by reference in its entirety herein. The mechanical arm of this type is manufactured by Leonard Medical, Inc., 1464 Holcomb Road, Huntington Valley, Pa. 19006. The surgeon D is able to view the procedure by reference to a monitor M, which displays the images captured by an endoscope and camera which are described in greater detail in concurrently filed U.S. application Ser. No. 10/280,489 entitled "Method of Securing Vertebrae;" International Patent Application PCT/US02/28106, filed Sep. 5, 2002, endoscope mount platform are described in U.S. patent application Ser. No. 09/491,808 filed Jan. 28, 2000, application Ser. No. 09/821,297 filed Mar. 29, 2001, and application Ser. No. 09/940,402 filed Aug. 27, 2001, the support arm and indexing collar are described in U.S. patent application Ser. No. 09/491,808 filed Jan. 28, 2000, application Ser. No. 09/821, 297 filed Mar. 29, 2001, and application Ser. No. 09/940,402 filed Aug. 27, 2001, which are incorporated by reference in their entirety herein. Alternatively, the surgeon D may view the surgical site though an eyepiece of the endoscope, or she may directly view the surgical site with loupes, microscope, or with the unaided eye.

The system and procedures will be described herein in connection with minimally invasive posterolateral spinal surgery. In particular, the procedure described herein is a posterolateral spine fusion involving an annulotomy and discectomy with the L4, L5 and S1 vertebrae. (In the drawings, the vertebrae will generally be denoted by reference letter V.) The usefulness of the inventive procedure is neither restricted to the posterolateral approach nor to the L4, L5 and S1 vertebra, but it may be used in other anatomical approaches and other vertebra within the cervical, thoracic and lumbar spine. The inventive procedure may be directed toward surgery involving one or more vertebral levels. It is also useful for anterior and lateral procedures. Moreover, it is believed that the invention is also particularly useful where any body structures must be protected from injury, and where it is desirable to provide sufficient space and visibility in order to manipulate surgical instrumentation and treat the underlying body structures.

The apparatus 100 is illustrated in FIGS. 2-6. The apparatus 100 includes an elongated body portion 102, which protects the nerve root or dura, and a mounting portion 104, which allows for the surgeon to releasably mount the apparatus 100 to a substantially stationary structure. Consequently, the surgeon is able to perform surgical procedures without requiring the surgeon or an assistant to continue to support the apparatus 100 throughout the procedure, and without reducing the field of view.

The apparatus 100 may be manufactured from a biocompatible material such as, but not limited to, stainless steel. In the exemplary embodiment, apparatus 100 is manufactured from stainless steel having a thickness of about 0.02 inches to about 0.036 inches. The elongated body portion 102 has dimensions which correspond to the depth in the body in which the procedure is being performed, and to the size of the body structure which is to be shielded by elongated body portion 102. In the exemplary embodiment, the elongated body portion 102 is a substantially flat rectangular portion having a width 106 of about 0.346 inches and a length 108 of about 5.06 inches (FIG. 3), although other dimensions would be appropriate for spinal surgical procedures performed at different locations, or for surgical procedures involving different body structures. The distal tip portion 110 of the apparatus 100 may have a slightly curved "bell mouth" configuration which allows for atraumatic contact with the body structure, such as a nerve.

The elongated body portion may be constructed according to several alternative embodiments. An additional exemplary embodiment is illustrated in FIG. 26, and described below.

Figure 3:
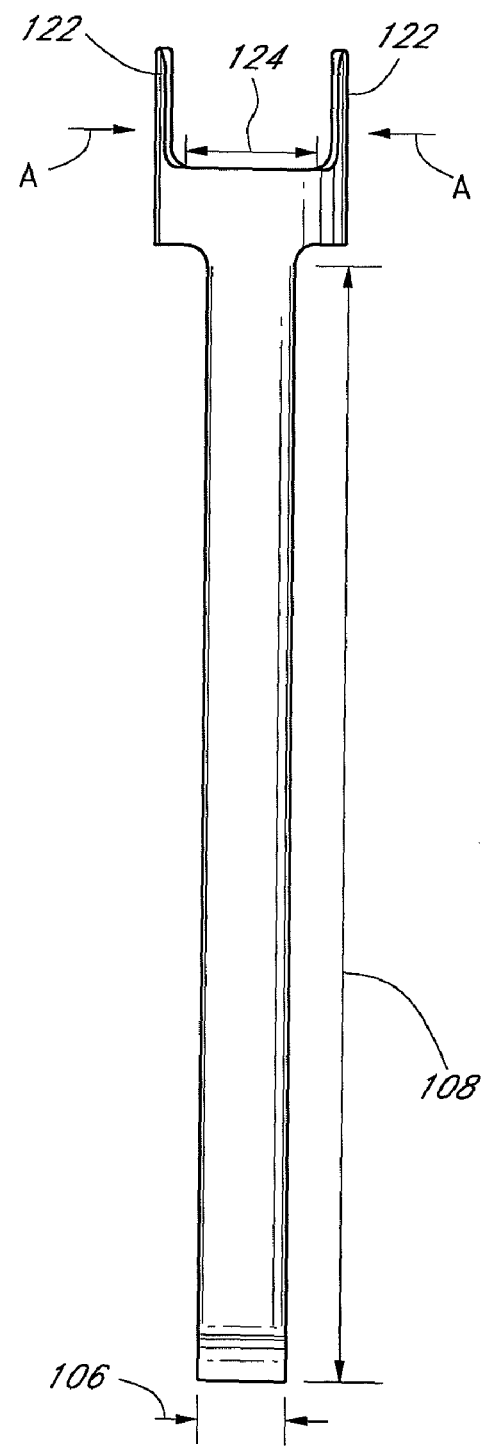
FIG. 3 is a front view of an apparatus in accordance with the present invention.
Figure 4:
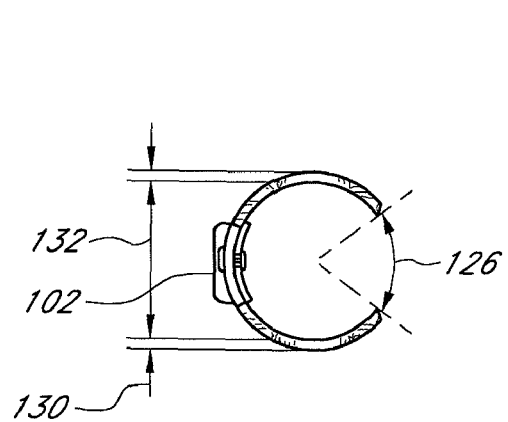
FIG. 4 is a top view of an apparatus in accordance with the present invention.
Figure 6:
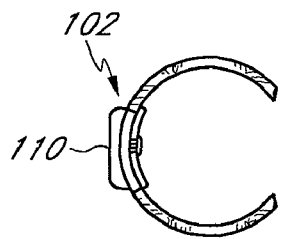
FIG. 6 is a bottom view of an apparatus in accordance with the present invention.
Figure 5:
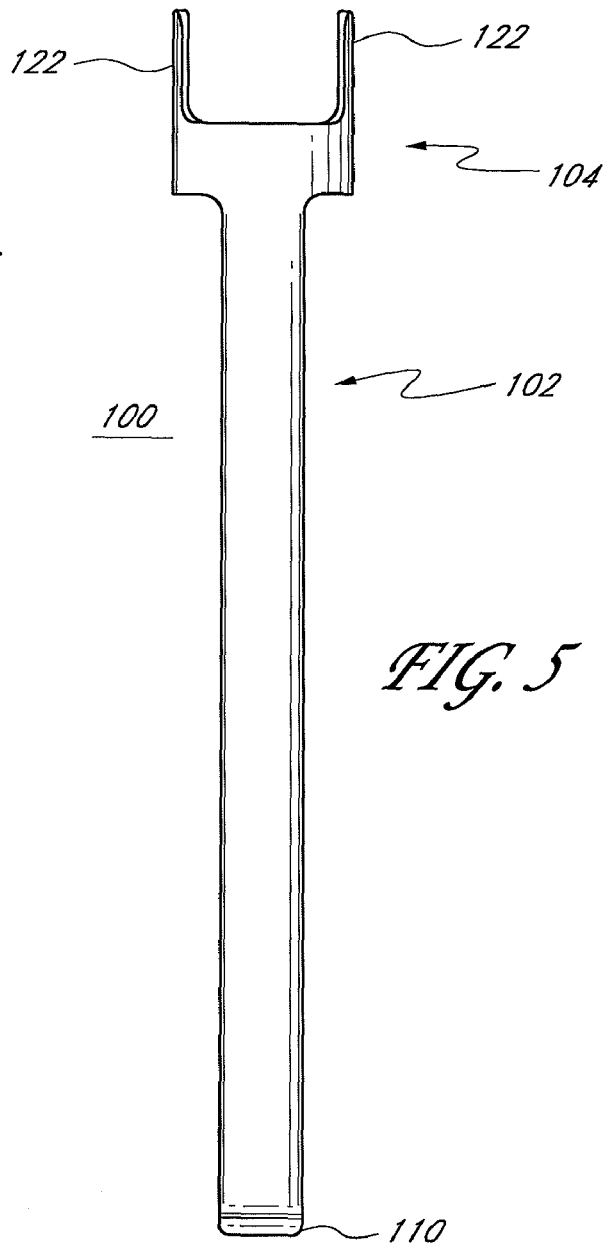
FIG. 5 is a back view of an apparatus in accordance with the present invention.

The mounting portion 104 allows the apparatus 100 to be secured to a support structure in any number of ways. In the exemplary embodiment, mounting portion 104 may include a ring portion. As seen in FIGS. 3, 4 and 6, ring portion 120 has a substantially ring-shaped configuration with an opening 124, which defines an angle 126 of about 90 degrees of the total circumference of the ring portion 120. As will be described in greater detail below, the angle 126 is a nominal value, because the ring portion 104 is resilient, which permits the opening 124 to change size during the mounting process.

In the exemplary embodiment, the mounting portion 104 has a substantially cylindrical configuration in order to be mounted within the interior lumen of a support structure, as will be described below. The ring portion 104 has an exterior dimension 130 of about 0.79 inches, and an interior dimension 132 of about 0.76 inches. It is understood that the dimensions of the ring portion 104 would be different if the expandable conduit has a different interior dimension. Moreover, the cylindrical shape of the ring portion 104 would change if the apparatus 100 is used with a support member having a differently shaped internal lumen.

Finger grip portions 122 extend from the mounting portion 104 and allow the surgeon to apply an inwardly directed force (as indicated by arrows A) to the ring portion 120. The resilient characteristics of the ring portion 120 allows the material to deflect thereby reducing the exterior dimension 130 and reducing the spacing 124. Releasing the finger grip portions 122 allows the ring portion to move towards its undeflected condition, thereby engaging the interior wall of the expandable conduit or other support structure, as will be described in greater detail below.

The elongated body portion 102 and the mounting portion 104 may be manufactured from a single component, such as a sheet of stainless steel, and then the mounting portion 104 may be subsequently formed into a substantially cylindrical shape. In another embodiment, the mounting portion 104 may be manufactured as a separate component and attached to the elongated body portion, by techniques such as, but not limited to welding and securement by fasteners, such as rivets.

Apparatus 100 is useful with a support structure, such as a conduit which provides an internal passage for surgical instrumentation to be inserted through the skin and muscle tissue of the patient P to the surgical site. The conduit serves as a support structure for supporting the apparatus 100, as will be described herein. The conduit may have a substantially constant cross-sectional area. According to an exemplary embodiment, the conduit has a wall portion defining a reduced profile configuration for initial percutaneous insertion into the patient. This wall portion may have a generally tubular configuration that may be passed over a dilator that has been inserted into the patient to atraumatically enlarge an opening sufficiently large to receive the conduit therein.

The wall portion of the conduit is subsequently expanded to an enlarged configuration, by moving against the surrounding muscle tissue to at least partially define an enlarged surgical space in which the surgical procedures will be performed. In a sense, it acts as its own dilator or retractor. Typically, but not by way of limitation, the distal portion expands to a greater extent than the proximal portion, since the surgical procedures are to be performed at the surgical site adjacent the distal portion thereof.

While in the reduced profile configuration, the conduit defines a first unexpanded configuration. Thereafter, the conduit enlarges the surgical space defined thereby by engaging the tissue surrounding the conduit and displacing the tissue radially outwardly as the conduit expands. The conduit may be sufficiently rigid to displace such tissue during the expansion thereof. The conduit may be resiliently biased to expand from the reduced profile configuration to the enlarged configuration. In addition, the conduit may also be manually expanded with surgical instrumentation inserted therein.

Figure 7:
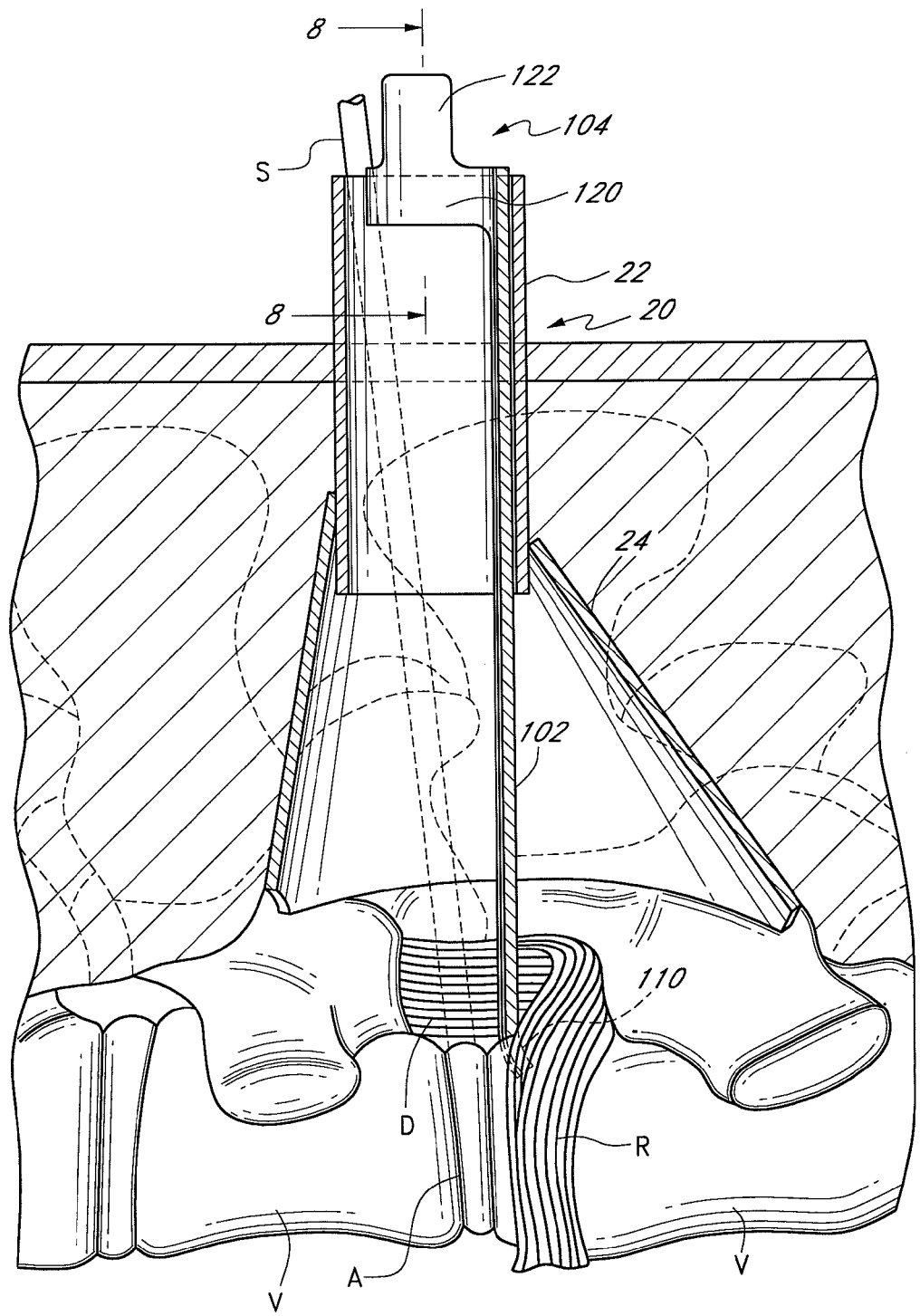
FIG. 7 is a sectional view of an apparatus, used in conjunction with additional structure in a patient, in accordance with the present invention.

An exemplary embodiment of the conduit, expandable conduit 20, is illustrated in FIG. 7. The expandable conduit 20 includes a proximal wall portion 22, which has a tubular configuration, and a distal wall portion, which is an expandable skirt portion 24. The skirt portion 24 is enlargeable from a reduced profile configuration (not shown), to an enlarged configuration. The skirt portion 24 may be attached to the proximal wall portion 22 with a rivet (not shown), pin, or similar connecting device to permit movement of the skirt portion 24 relative to the proximal cylindrical tube portion 22.

The skirt portion 24 may be sufficiently rigid that it is capable of displacing the tissue surrounding the skirt portion 24 as it expands. Depending upon the resistance exerted by surrounding tissue, the skirt portion may be sufficiently rigid to provide some resistance against the tissue to remain the configurations of FIGS. 3-4. Moreover, the expanded configuration of the skirt portion 24 is at least partially supported by the body tissue of the patient. The rigidity of the skirt portion 24 and the greater expansion at the distal portion creates a stable configuration that is at least temporarily stationary in the patient, which frees the surgeon from the need to actively support the conduit 20.

In the exemplary embodiment, the access point for beginning the surgical procedure corresponds to the posterior-lateral aspects of the spine. Placement of the expandable conduit 20 is preferably midway (in the ceph-caud direction) between the L4 through S1 vertebrae, centrally about 4-7 cm from the midline. An incision is made at the above-determined location. A guide wire (not shown) is introduced under fluoroscopic guidance through the skin, fascia, and muscle to the approximate surgical site. A series of dilators is used to sequentially expand the incision to the desired width, about 23 mm for the exemplary procedure, without damaging the structure of surrounding tissue and muscles. Following placement of the largest dilator, the expandable conduit 20, in its reduced profile configuration (not shown), is introduced and positioned in a surrounding relationship over the dilator. The dilator is subsequently removed from the patient, and the expandable conduit 20 is allowed to remain in position.

Once the expandable conduit 20 is positioned in the patient, it may be enlarged to provide a passage for the insertion of apparatus 100 and various surgical instrumentation and an enlarged surgical space for performing the procedures described herein. In the exemplary procedure, the expandable conduit 20 may be expanded by removing a suture and tearing a sleeve surrounding the expandable conduit 20, and subsequently allowing the skirt portion 24 to resiliently expand towards its fully expanded configuration as to create an enlarged surgical space from the L4 to the S1 vertebrae. Under many circumstances, the space created by the skirt portion 24 in the intermediate configuration is a sufficiently large working space to perform the procedure described herein. Once the skirt portion 24 has expanded, the rigidity and resilient characteristics of the skirt portion 24 allow the conduit 20 to resist closing to the reduced profile configuration of FIG. 2 and to at least temporarily resist being expelled from the incision. These characteristics create a stable configuration for the conduit 20 to remain in position in the body, supported by the surrounding tissue. Thus the conduit 20 acts as a retractor to position the body tissue away from the surgical space.

Further details of the expandable conduit are described in U.S. Pat. No. 6,187,000, and in International Patent Application PCT/US02/28106, filed Sep. 5, 2002, U.S. patent application Ser. No. 09/772,605, filed Jan. 30, 2001, U.S. application Ser. No. 09/855,358 filed May 15, 2001, and U.S. application Ser. No. 09/630,077 filed Aug. 1, 2000, which are incorporated by reference in their entirety herein.

Once the expandable conduit 20 is in position, debridement and decortication of tissue covering the vertebrae may be performed. In order to access the disc A, the outer bone portions of the vertebrae may be cut away. For example, a facetecomy/laminectomy may be performed using standard instrumentation, e.g., kerrisons, osteotomes, curettes, rongeurs, and a high speed burr. These instruments (not shown) are substantially identical to those used in standard open procedures. However, these instruments are typically modified with elongated handles for use in connection with the expandable conduit 20.

The expandable conduit 20 serves as a stable mounting structure for apparatus 100. In particular, mounting portion 104 is releasably mounted to the interior wall of proximal wall portion 22 of expandable conduit 20. Elongated body portion 102 extends distally into the operative site to protect the desired body structure, such as the nerve, as will be described below.

To install the apparatus 100 within the interior passage of the proximal wall portion 22, the surgeon may apply an inwardly directed force on the finger grip portions 122, thereby causing the ring portion 120 to resiliently deform, as illustrated by dashed line and arrows B in FIGS. 8-9. The surgeon subsequently inserts the apparatus 100 into the interior lumen of the proximal wall portion 22 (as indicated by arrow C) to the position of ring portion 104 illustrated in solid line in FIGS. 8-9. When the surgeon releases the finger grip portions 122, the ring portion 120 resiliently moves towards its undeflected configuration, thereby engaging the interior lumen of the proximal wall portion 122. The mounting portion 104 described herein has the advantage that it is easily removed and/or moved with respect to the conduit 20 without disturbing the position of the conduit 20 or any other instrumentation. In particular, the mounting portion 104 may be released from the interior lumen of the proximal wall portion 22 by applying an inwardly directed force on the finger grip portions 122, as illustrated in FIG. 8.

As illustrated in FIGS. 7 and 9, the configuration of the mounting portion 104 and the elongated body portion 102 allow the elongated body portion 102 to occupy a small space along the periphery of the proximal wall portion 122. This allows the apparatus to protect the desired body structure without blocking access for the insertion of other surgical instrumentation, and without blocking visibility by the surgeon during the procedure.

The mounting portion 104 is one exemplary configuration for mounting the apparatus to the support structure. Additional exemplary embodiments of the mounting portion are illustrated in FIGS. 16-21, and described below.

When in position, the distal end portion 110 covers the exiting nerve root R, while exposing the disc annulus A (See FIG. 7). As discussed above, the debridement and decortication of tissue covering the vertebrae, as well as a facetecomy and/or laminectomy if indicated, are performed prior to the insertion of apparatus 100 into the surgical space. Thus, there is no need to displace or retract tissue, and apparatus 100 merely covers the nerve root and does not substantially displace the nerve root or any other body tissue. It is understood that term "cover" as used herein refers to apparatus 100 being a small distance adjacent to the body structure, or in contact with the body structure without applying significant tension or displacement force to the body structure.

Additional surgical instrumentation S may be inserted to the expandable conduit to perform procedures on the surrounding tissue. For example, an annulotomy may be performed using a long handled knife and kerrisons. A discectomy may be completed by using curettes and rongeurs. Removal of osteophytes which may have accumulated between the vertebrae may be performed using osteotomes and chisels.

Figure 10:
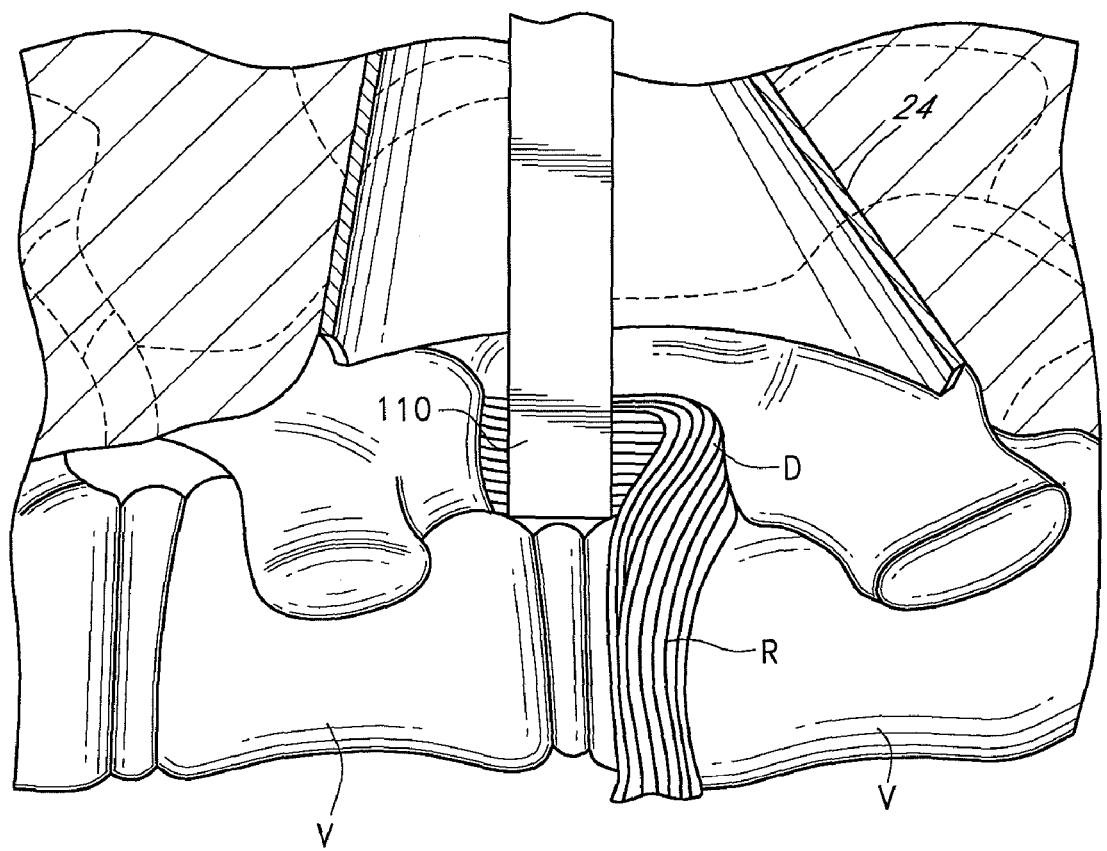
FIG. 10 is a sectional view, similar to FIG. 7, illustrating an alternative position of the apparatus in accordance with the present invention.

As illustrated in FIG. 10, the elongated body portion 102 is rotated to protect the spinal cord, or dura D, during the above procedures. The surgeon may change the position of the apparatus 10 by approximating the finger grips 122 to release the ring portion from engagement with the inner wall of the proximal wall portion 20, and then re-position the apparatus 100 without disturbing the expandable conduit 20 (as shown in FIG. 8).

Figure 11:
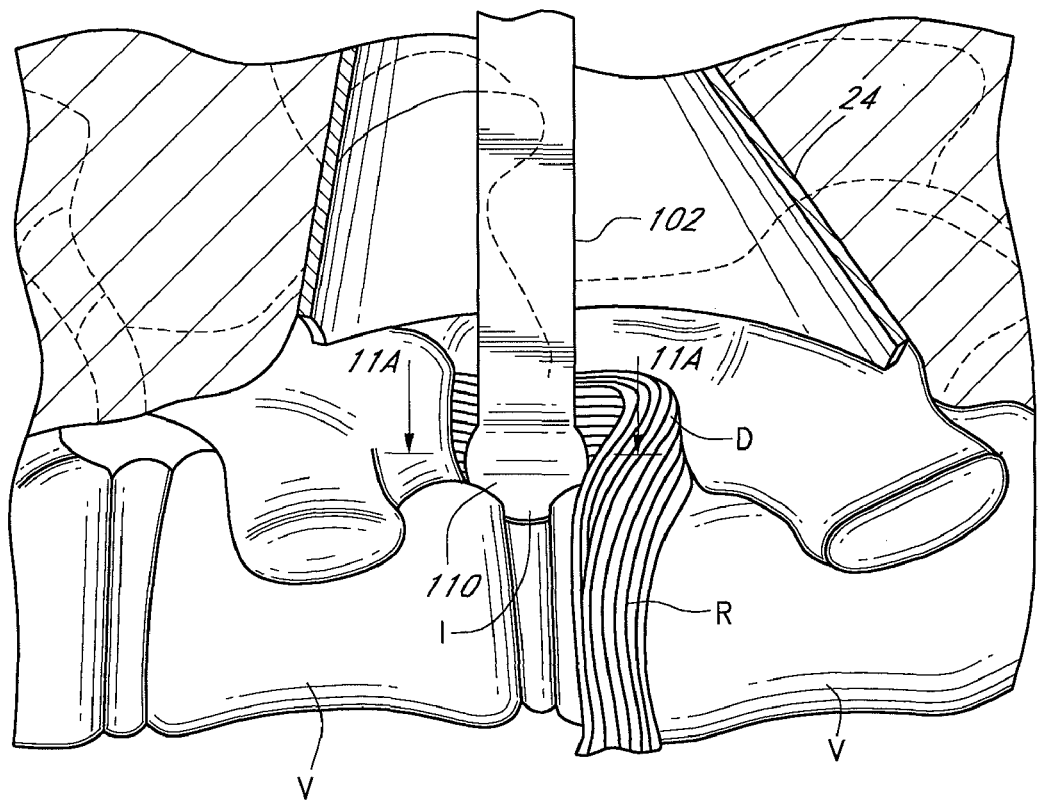
FIG. 11 is a sectional view, similar to FIG. 7, illustrating another alternative position of the apparatus in accordance with the present invention.
Figure 11A:
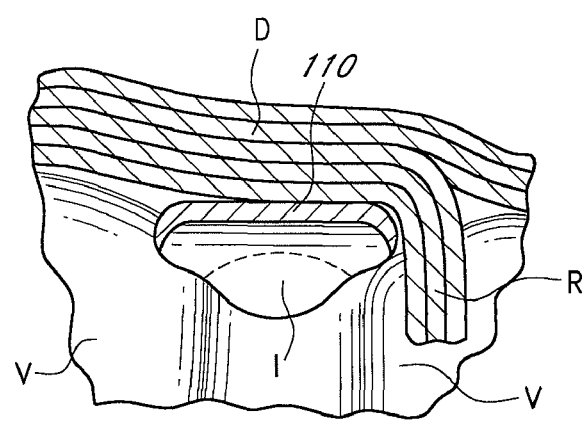

During certain surgical procedures, it may be useful to introduce crushed bone fragments, solid bone spacers, or other material to promote bone fusion and stabilize the spine. As illustrated in FIGS. 11-11(a), apparatus 100 is useful to direct the material into the space I between adjacent vertebrae V. As shown in the figures, the distal portion 110 of the elongated body portion 102 is partially inserted into the space I. The distal end portion 110, is positioned between adjacent vertebrae V, and creates a partially enclosed space for receiving the crushed bone fragments or other material therein.

Another embodiment of the apparatus is illustrated in FIGS. 12-13, and designated apparatus 200. Apparatus 200 is substantially identical to apparatus 100, described above, with the following differences noted herein. In particular, distal end portion 210 includes a pair of surfaces 240 and 242. Surface 240 is an extension of elongated shield portion 202, and surface 242 extends at an angle with respect to surface 240. In the exemplary embodiment, surfaces 240 and 242 defined an angle of about 45° to about 90° between them. Alternatively another angle between surfaces 240 and 242 may be defined as indicated by the body structures to be protected.

Figure 14:
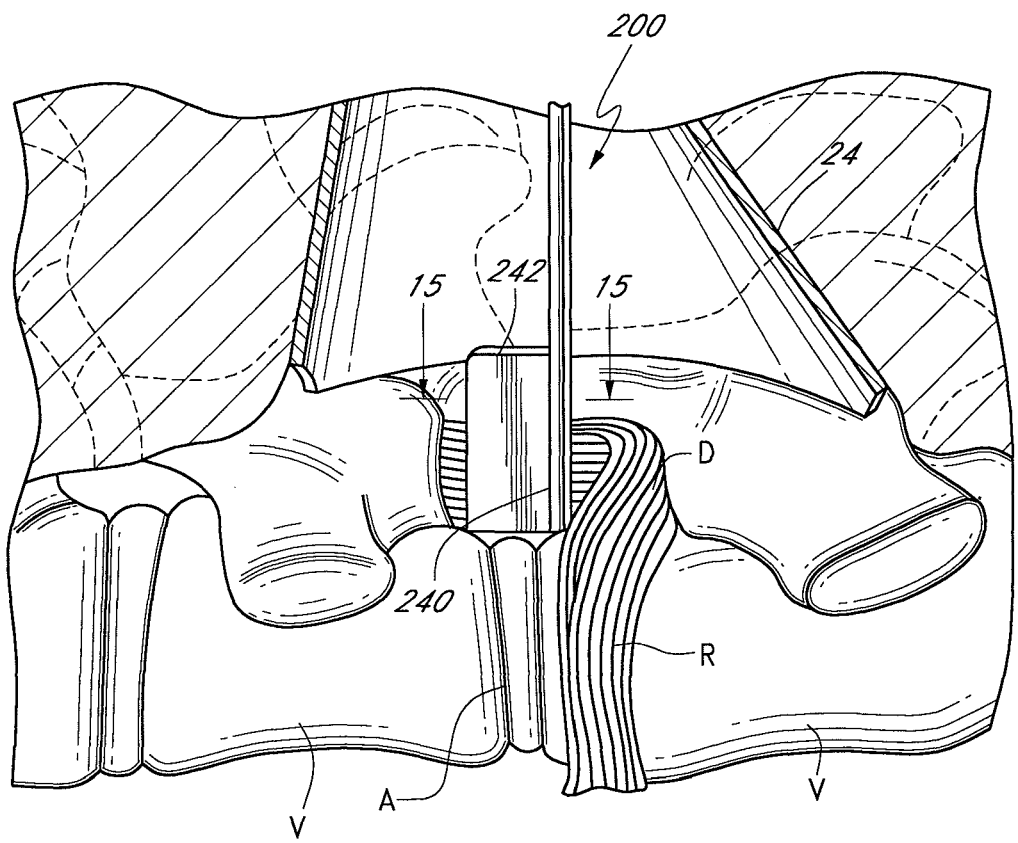
FIG. 14 is a sectional view, similar to FIG. 7, of the embodiment of FIGS. 12-13, used in conjunction with additional structure in a patient, in accordance with the present invention.
Figure 15:
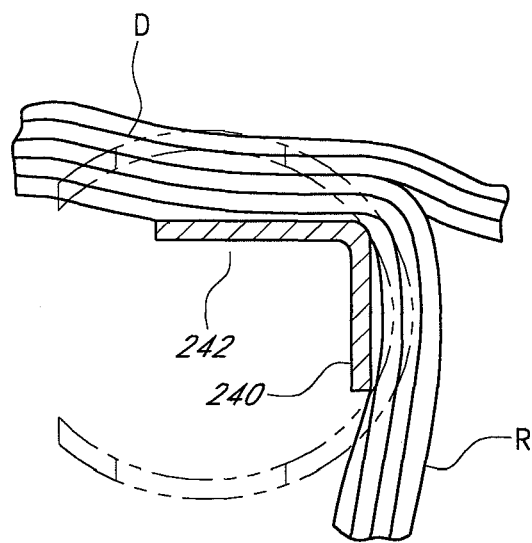
FIG. 15 is a transverse sectional view of the apparatus of FIGS. 12-13, taken along lines 13-13 of FIG. 14, in accordance with the present invention.

As illustrated in FIGS. 14-15, distal end portion 210 allows the apparatus to provide simultaneous shielding of both the dura D and the nerve root R. In FIGS. 14-15, surface 242 shields the dura D, and surface 240 shields the nerve root R. It is understood that surfaces 240 and 242 may be interchange with respect to which tissue they protect during the surgical procedure.

After spinal fixation, or another surgical procedure, is completed, the surgical instrumentation, including apparatus 100 (or apparatus 200, as appropriate), is withdrawn from the surgical site. Surgical apparatus 100 may be released from the interior lumen of the proximal wall portion 22 by applying an inwardly directed force to the finger grip portions 122, as described above. The expandable conduit 20 is also withdrawn from the site. The muscle and fascia typically close as the expandable conduit 20 is withdrawn through the dilated tissues in the reduced profile configuration. The fascia and skin incisions are closed in the typical manner, with sutures, etc. The procedure described above may be repeated for the other lateral side of the same vertebrae, if indicated.

Figure 16:
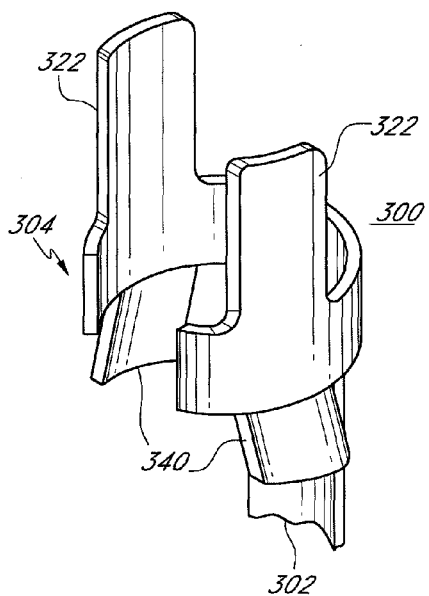
FIG. 16 is a perspective view of a portion of another embodiment of the apparatus in accordance with the present invention.
Figure 17:
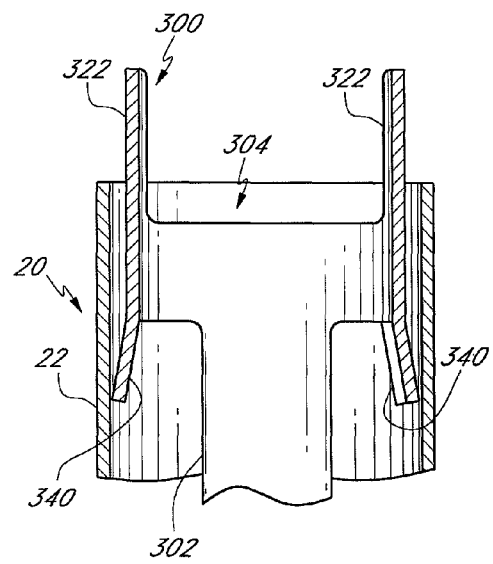
FIG. 17 is a longitudinal section view of the apparatus of FIG. 16 in accordance with the present invention.

Additional embodiments of the apparatus are described herein. Apparatus 300 is substantially identical to apparatus 100, with the following differences noted herein. The mounting portion 304 of apparatus 300 may have an external diameter which is smaller than the internal diameter of the cannula, e.g., proximal wall portion 22 of expandable conduit 20 (FIG. 17). As illustrated in FIGS. 16-17, mounting portion 304 is provided with a pair of flanges 340, which have a component that extends at least partially radially outwardly. When positioned within the interior of proximal wall portion 22 (in a manner substantially as described above in connection with FIG. 8, the flanges 340 engage the interior of proximal conduit 22, thereby retaining the apparatus 300 in position.

Figure 18:
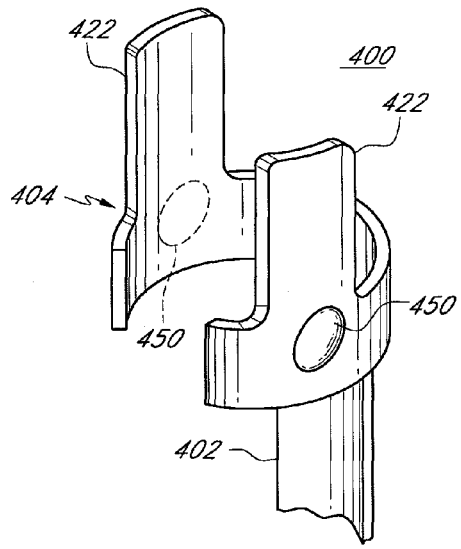
FIG. 18 is a perspective view of a portion of yet another embodiment of the apparatus in accordance with the present invention.
Figure 19:
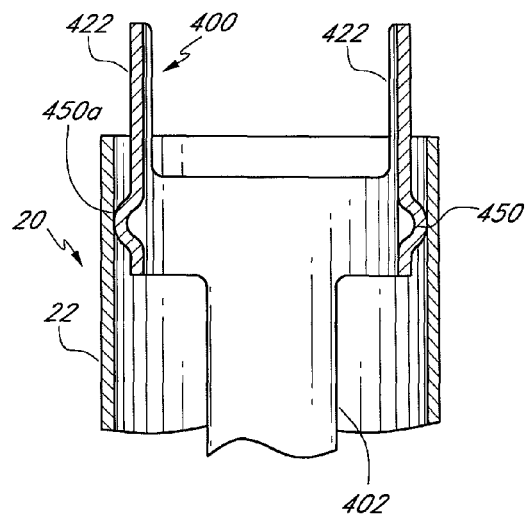
FIG. 19 is a longitudinal section view of the apparatus of FIG. 18 in accordance with the present invention.

Similarly, apparatus 400 is substantially identical to apparatus 100, with the following differences noted herein. The mounting portion 404 of apparatus 400 may also have an external diameter which is smaller than the internal diameter of the cannula, e.g., proximal wall portion 22 of expandable conduit 20 (FIG. 19). As illustrated in FIGS. 18-19, mounting portion 404 is provided with a pair of bumper members 450, which may be manufactured from a material such as neoprene (Buna-N). When positioned within the interior of proximal wall portion 22 (substantially as described above in connection with FIG. 8, the bumper members 450 engage the interior of proximal conduit 22, thereby retaining the apparatus 400 in position. According to another embodiment, the bumper members may alternatively be a pair of dimples 450a formed in the material of the mounting portion 402 (left side of FIG. 19). (For illustrative purpose, FIG. 19 shows a bumper member 450 on the right side and a dimple 450a on the left side of the mounting member 404. Without limiting the above, it is understood that mounting member 404 may be provided with a pair of bumper members 450 or a pair of dimples 450a to engage the interior lumen of proximal wall portion 22.)

Figure 20:
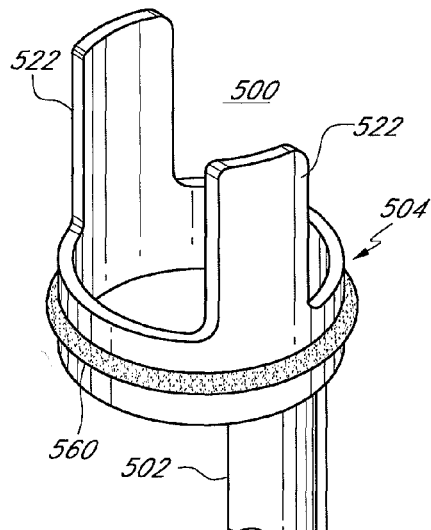
FIG. 20 is a perspective view of a portion of a further embodiment of the apparatus in accordance with the present invention.
Figure 21:
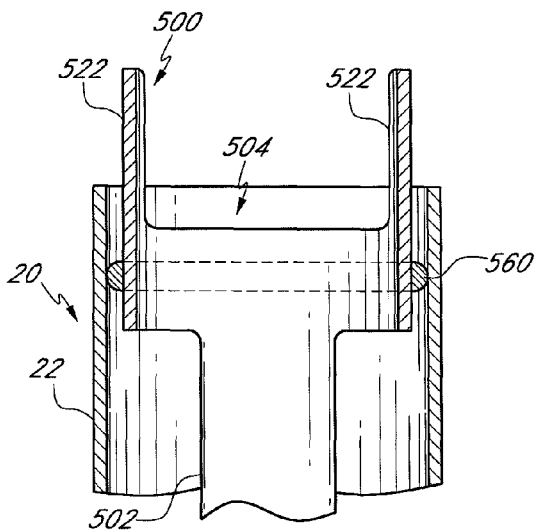
FIG. 21 is a longitudinal section view of the apparatus of FIG. 20 in accordance with the present invention.
Figure 22:
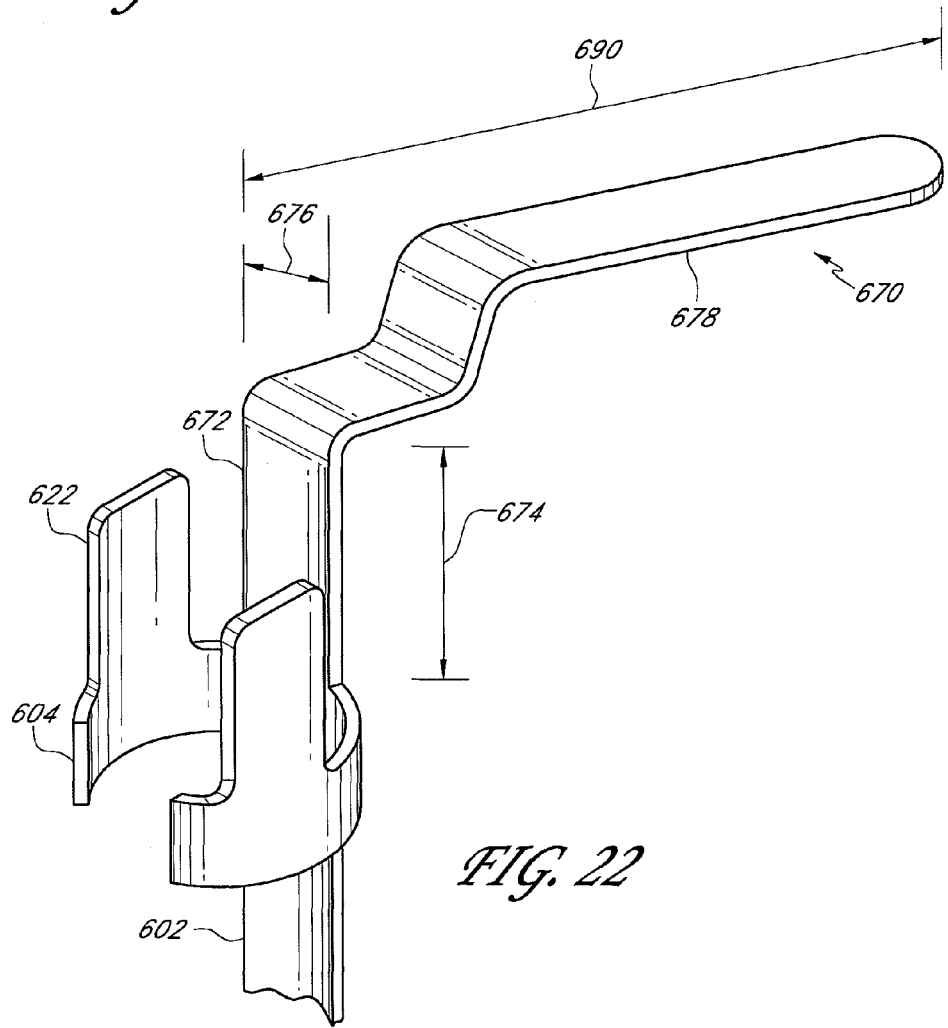
FIG. 22 is a perspective view of a portion of a still further embodiment of the apparatus in accordance with the present invention.

Apparatus 500 is also substantially identical to apparatus 100, with the following differences noted herein. The mounting portion 504 of apparatus 500 may also have an external diameter which is smaller than the internal diameter of the cannula, e.g., proximal wall portion 22 of expandable conduit 20 (FIG. 21). As illustrated in FIG. 20, mounting portion 504 may be either a closed ring (as shown) or a split ring (not shown, similar to ring portion 122) which is provided with an O-ring 560 (or a C-ring in the case of a split-ring configuration), which may be manufactured from a material such as neoprene (Buna-N). When positioned within the interior of proximal wall portion 22 (in a manner substantially as described above in connection with FIG. 8, the O-ring 560 engages the interior of proximal wall portion 22, thereby retaining the apparatus 400 in position.

Apparatus 600 is another embodiment, which is substantially identical to apparatus 100, with the following differences noted herein. Apparatus 600 is further provided with a handle portion 670. Handle portion 670 provides additional leverage and visibility to the apparatus during the procedure. According to an exemplary embodiment, the handle portion 670 is integral with the mounting portion 604. The handle portion 670 may comprise a longitudinally extending portion 672 which may have a length 674 of about 1 to about 2 inches, and a width 676 of about ¼ inch to about ½ inch. The handle portion 6670 may further comprise a laterally extending portion 678 that may extend a length 680 of about 3 to about 5 inches from the center of the apparatus 600. Other dimensions may be appropriate as required by the body structures being protected by apparatus 600.

Further embodiments of the invention are illustrated in FIGS. 23-25. Apparatus 700 and 800 are substantially identical to apparatus 100, with the following differences noted herein. For example, apparatus 700 is provided with tab 780 which extends from the body portion 702. The tab 780 may be located at any location along the length of the body portion 702. As illustrated in FIG. 24, tab 780 is substantially cylindrical in shape and may extend about ¼ inch from the body portion 702. A pair of graspers G (illustrated in dashed line), or other surgical instrumentation, may be used to engage the tab 780 and remotely reposition the distal end portion 710 with respect to the support structure and the body structure during the procedure. Apparatus 800 incorporates a tab 880 which is fabricated from body portion 802 by making a "U"-shaped cut in the material of body portion 802 and bending the tab 880 into the position illustrated in FIG. 26

Figure 27:
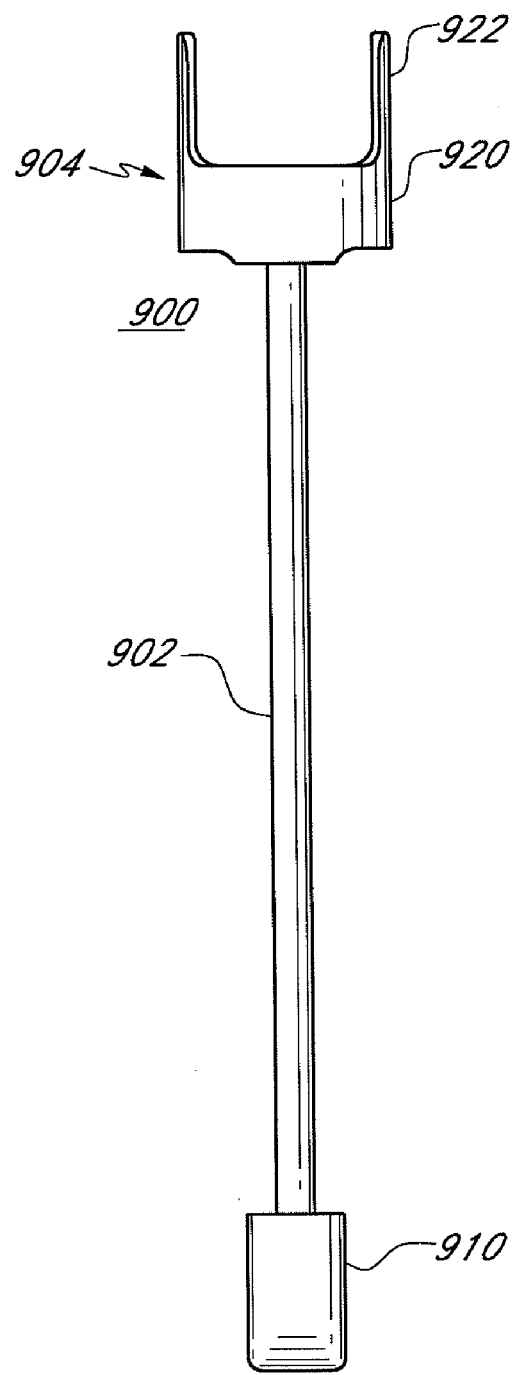
FIG. 27 is a front view of another embodiment of an apparatus.

Apparatus 900 (see FIG. 27) is substantially identical to apparatus 100; however, the body portion 902 may be fabricated from a rod portion which supports the distal end portion 910.

It will be understood that the foregoing is only illustrative of the principles of the invention, and that various modifications can be made by those skilled in the art without departing from the scope and spirit of the invention. For example, the apparatus has been described in connection with an expandable conduit. The apparatus also finds useful application in other minimally invasive procedures, such as with a constant diameter or cannula, or in conventional, open procedures.

What is claimed is:

1. System for shielding a body structure during surgical procedures comprising:
   a) an expandable conduit comprising a wall portion defining an internal passage therethrough and a first configuration having a first cross-sectional area at a distal portion thereof for percutaneous insertion into said body tissue, said wall portion movable to define a second configuration having an enlarged cross-sectional area at said distal portion thereof; and
   b) a shield apparatus configured for insertion into said internal passage of said expandable conduit, comprising
      i) an elongated body portion comprising an atraumatic distal tip portion configured to at least partially cover said body structure without substantially displacing said body structure;
      ii) a mounting portion at a proximal end portion thereof for mounting said shield apparatus to said internal passage of said wall portion; and
      iii) a member connected to said mounting portion to release said mounting portion with respect to said internal passage of said wall portion.

2. The system as recited in claim 1, wherein said mounting portion comprises a ring-shaped configuration defining a gap.

3. The system as recited in claim 2, wherein said mounting portion comprises a resilient material.

4. The system as recited in claim 3, wherein said mounting portion is resiliently movable between a first configuration having a first outer dimension and a second configuration having a second, reduced outer dimension.

5. The system as recited in claim 3, wherein said member comprises a pair of finger grips extending from said ring-shaped portion for deforming said mounting portion to said second configuration.

6. The system as recited in claim 1, wherein said mounting portion further comprises a flange configured to engage said internal passage of said expandable conduit.

7. The system as recited in claim 1, wherein said mounting portion further comprises a bumper member configured to engage said internal passage of said expandable conduit.

8. The system as recited in claim 1, wherein said mounting portion further comprises an O-ring member configured to engage said internal passage of said expandable conduit.

9. The system as recited in claim 1, wherein said body structure is a nerve located adjacent vertebral tissue, and wherein said distal tip portion is configured to cover the nerve root without substantially displacing the nerve root.

10. The system as recited in claim 1, wherein said body structure is the dura, and wherein said distal tip portion is configured to cover the dura without substantially displacing the dura.

11. The system as recited in claim 1, wherein said body structure is the dura and adjacent vertebrae, and wherein said distal tip portion is configured to be positioned adjacent the dura and between the vertebrae to define a space for receiving material therein.

12. The system as recited in claim 1, wherein said distal tip portion comprises a pair of surfaces defining an angle therebetween.

13. The system as recited in claim 12, wherein said distal tip portion is configured to engage the nerve root and the dura.

14. The system as recited in claim 12, wherein said angle between said pair of distal surfaces is about 45-90 degrees.

15. The system as recited in claim 1, wherein the elongated body portion comprises a substantially flat, rectangular member.

16. The system as recited in claim 1, wherein the elongated body portion comprises a rod.

17. The system as recited in claim 1, wherein the shield apparatus further comprises a handle portion.

18. The system as recited in claim 1, wherein the shield apparatus further comprises a tab portion extending from the elongated body portion and configured to be engaged by an instrument to reposition said distal end portion of said shield apparatus.

19. The system as recited in claim 18, wherein the tab portion is a substantially cylindrical member fixed to the elongated body portion.

20. The system as recited in claim 18, wherein the tab portion is a flange portion integral with the elongated body portion.

21. System for shielding a body structure during surgical procedures comprising:
   a) an expandable conduit comprising a wall portion having a proximal portion and a distal portion, said expandable conduit defining an access path therethrough, said wall portion being capable of movement from a first contracted position having a first cross-sectional area at said distal portion to a second expanded position having an enlarged cross-sectional area at said distal portion; and b) a shield apparatus configured for insertion into said access path of said expandable conduit, comprising
   i) an elongated body portion comprising a distal portion configured to at least partially cover said body structure without substantially displacing said body structure;
   ii) a mounting portion at a proximal end portion thereof for mounting said shield apparatus to said proximal portion of said wall portion, said mounting portion configured to position said elongated body to shield said body structure; and
   iii) an engagement member connected to said mounting portion to engage said mounting portion to said proximal portion of said wall portion and to release said mounting portion with respect to said proximal portion of said wall portion.

22. The system as recited in claim 21, wherein the shield apparatus further comprises a handle portion.

23. The system as recited in claim 21, wherein the shield apparatus further comprises an extended portion extending from the elongated body portion and configured to be engaged by an instrument to reposition said distal end portion of said shield apparatus.

24. The system as recited in claim 23, wherein the extended portion is a flange portion integral with the elongated body portion.

25. The system as recited in claim 21, wherein the elongated body portion is substantially flat and has a substantially rectangular cross-section.

26. The system as recited in claim 21, wherein an inner surface of the wall portion is concave.

27. The system as recited in claim 21, wherein said mounting portion is configured to mount said elongated body in a variety of positions relative to said wall portion to shield said body structure.

28. The system as recited in claim 27, wherein said engagement member is configured to allow the shield apparatus to be engaged with the wall portion, released, re-positioned, and re-engaged with the wall portion while the expandable conduit remains stationary.

29. The system as recited in claim 21, wherein the expandable conduit has a substantially tubular configuration in the contracted position.

30. The system as recited in claim 21, wherein the cross-sectional area of said wall portion at a first location is greater than the cross-sectional area of said wall portion at a second location in the expanded position, wherein the first location is distal to the second location.

31. The system as recited in claim 21, wherein the access path is sized such that additional surgical instruments can be advanced along the access path between the proximal and distal portions when the shield apparatus is positioned within the expandable conduit.

32. The system as recited in claim 21, wherein at least the distal portion of the wall portion is sufficiently rigid to displace tissue as it expands.

33. A system for shielding a body structure while providing access to a surgical site during a surgical procedure, comprising:

a) an expandable conduit having a proximal end and a distal end and defining a length therebetween such that the proximal end can be positioned outside the patient and the distal end can be positioned inside the patient adjacent the surgical site, said expandable conduit having a wall portion with an inner surface defining an access path, said expandable conduit being expandable from a contracted configuration to an expanded configuration, wherein the cross-sectional area of the conduit at a first location is greater than the cross-sectional area of the conduit at a second location in the expanded configuration, wherein the first location is distal to the second location; and b) a shield apparatus configured for insertion into the access path of the expandable conduit, comprising
   i) an elongated body portion comprising a distal tip portion configured to at least partially shield said body structure;
   ii) a mounting portion at a proximal end portion of the elongated body portion for mounting the shield apparatus to the proximal end of the expandable conduit; and
   iii) a member connected to the mounting portion to release the mounting portion with respect to the proximal end of the expandable conduit.

* * * * *